US005726320A

United States Patent [19]

Robey

[11] Patent Number: 5,726,320
[45] Date of Patent: Mar. 10, 1998

[54] PREPARATION OF BICYCLOHEXANE DERIVATIVE

[75] Inventor: Roger Lewis Robey, Greenwood, Ind.

[73] Assignee: Eli Lilly and Company, Indianapolis, Ind.

[21] Appl. No.: 672,491

[22] Filed: Jun. 26, 1996

Related U.S. Application Data

[60] Provisional application No. 60/000,642 Jun. 29, 1995.

[51] Int. Cl.$^6$ .................. C07D 235/02; C07D 487/20; C07C 61/12; C07C 61/28; A61K 31/415
[52] U.S. Cl. .................. 548/301.4; 562/5; 562/500; 562/501; 562/509; 514/393
[58] Field of Search .................. 548/301.4; 562/500, 562/501, 509

[56] References Cited

U.S. PATENT DOCUMENTS

| | | | |
|---|---|---|---|
| 2,560,584 | 7/1951 | McDonald | 548/301.4 X |
| 2,629,660 | 2/1953 | Harsh | 548/301.4 X |
| 2,732,380 | 1/1956 | Reppe et al. | 548/301.4 |
| 2,762,708 | 9/1956 | Mackey | 548/301.4 |
| 3,271,245 | 9/1966 | Cremlyn et al. | 548/301.4 X |
| 3,532,744 | 10/1970 | Fletcher et al. | 548/301.4 |
| 3,594,413 | 7/1971 | Alburn et al. | 548/500 X |
| 3,704,312 | 11/1972 | Russel et al. | 548/301.4 |
| 3,716,553 | 2/1973 | Alburn et al. | 548/301.4 |
| 3,725,423 | 4/1973 | Rynbrandt | 564/290 X |
| 3,746,495 | 7/1973 | Malis et al. | 562/500 |
| 3,823,177 | 7/1974 | Fanta et al. | 562/500 X |
| 4,315,031 | 2/1982 | Vincent et al. | 424/309 |
| 4,320,135 | 3/1982 | Kathawala | 548/301.4 X |
| 4,861,913 | 8/1989 | Narisada et al. | 562/427 |
| 5,228,898 | 7/1993 | Ueda et al. | 504/348 |

FOREIGN PATENT DOCUMENTS

| | | | |
|---|---|---|---|
| WO 95/15940 | 6/1995 | European Pat. Off. | 562/500 X |
| 0696577 | 2/1996 | European Pat. Off. | 562/500 |
| 0802158 | 2/1951 | Germany | 562/500 |

OTHER PUBLICATIONS

Y. Nakagawa et al., "(2S,3S,4S)α-(Carboxycyclopropyl)-glycine is a novel agonist of metabotropic glutamate receptors," *European J. Pharmacology*, 184, 205-206 (1990).

Y. Hayashi et al., "Agonist analysis of 2-(carboxycyclopropyl)glycine isomers for cloned metabotropic glutamate receptor subtypes expressed in Chinese hamster ovary cells," *Br. J. Pharmacol.*, 107, 539-543 (1992).

H. Shinozaki and M. Ishida, "Recent Advances in the Study of Glutamate Receptor Agonists," *Asia Pacific J. of Pharmacol.*, 6, 293-316 (1991).

F. Nicoletti et al., "(2s, 1'$_R$, 2'$_R$, 3'$_R$)-2-(2,3-Dicarboxycyclopropyl)glycine enhances quisqualate-stimulated inositol phospholipid hydrolysis in hippocampal slices," *Eur. J. Pharmacol.-Molecular Pharmacol. Section*, 245, 297-298 (1993).

M. Ishida et al., "A potent metabotropic glutamate receptor agonist: electrophysiological actions of a conformationally restricted glutamate analogue in the rat spinal cord and Xenopus oocytes," *Brain Res.*, 537, 311-314 (1990).

M. Ishida et al., "A novel metabotropic glutamate receptor agonist: marked depression of monosynaptic excitation in the newborn rat isolated spinal cord," *Br. J. Pharmacol.*, 109, 1169-1177 (1993).

V. Bruno et al., "Protective effect of the metabotropic glutamate receptor agonist, DCG-IV, against excitotoxic neuronal death," *Eur. J. Pharmacol.*, 256, 109-112 (1994).

H. Kaba et al., "Induction of an Olfactory Memory by the Activation of a Metabotropic Glutamate Receptor," *Science*, 265, 262-264 (Jul. 8, 1994).

D.E. Jane et al., "Actions of two new antagonists showing selectively for different sub-types of metabotropic glutamate receptor in the neonatal rat spinal cord," *Br. J. Pharmacol.*, 112, 809-816 (1994).

F. Nicoletti et al., "Effect of Metabotropic Glutamate Receptor Agonists on Excitotoxic or Apoptotic Neuronal Degeneration," *Neuropschychopharmacology*, 10 (3S), 623S (1994).

J. Greenstein et al, "Chemistry of the Amino Acids", John Wiley & Sons, Inc (New York), 6, 2559-2567 (1961).

D.D. Schoepp, et al., *European Journal of Pharmacology*, vol. 207, 1991, pp. 351-353.

G. Costantino, et al., "Definition of a Pharmacophore for the Metabotropic Glutamate Receptors Negatively Linked to Adenylyl Cyclase", *Bioorganic & Medicinal Chemistry*, 1, 259-265 (1993).

Primary Examiner—Floyd D. Higel
Attorney, Agent, or Firm—Martin A. Hay; David E. Boone

[57] ABSTRACT

A process for the preparation of (+)-2-amino-bicyclo[3.1.0]-hexane-2-6-dicarboxylic acid, or a pharmaceutically acceptable salt thereof, which comprises hydrolysing (−)-2-spiro-5'-hydantoinbicyclo[3.1.0]hexane-6-carboxylic acid or a salt thereof, and optionally forming a pharmaceutically acceptable salt. Also disclosed are intermediates useful in the process.

10 Claims, No Drawings

PREPARATION OF BICYCLOHEXANE DERIVATIVE

This application claims the benefit of U.S. provisional Application No. 60/000,642, filed Jun. 29, 1995.

The present invention relates to the preparation of (+)-2-aminobicyclo[3.1.0]hexane-2,6-dicarboxylic acid, or a pharmaceutically acceptable salt thereof.

(+)-2-Aminobicyclo[3.1.0]hexane-2,6-dicarboxylic acid is a novel agonist at negatively coupled cAMP-linked metabotropic glutamate receptors. It is useful for the treatment of neurological and psychiatric disorders linked to excitatory amino acid receptors, for example anxiety disorders, drug tolerance, withdrawal and cessation, and smoking cessation. The compound, its properties and methods for preparing it (including the subject matter claimed in the present application) are described in detail in European Patent Application Publication No. 696,577 and equivalent applications, which were all published after the priority date of the present application. European Patent Application Publication No. 696,577 and the equivalent applications claim priority from U.S. patent application Ser. No. 08/289,957, filed Aug. 12, 1994, and now abandoned, U.S. patent application Ser. No. 08/337,349, filed Nov. 10, 1994, and now abandoned, and U.S. patent application Ser. No. 08/496,643, filed Jun. 29, 1995. The subject matter claimed in the present application was first described in U.S. patent application Ser. No. 08/496,643, filed Jun. 29, 1995, and in the priority application for the present application, also filed Jun. 29, 1995.

According to one aspect, the present invention provides a process for the preparation of (+)-2-aminobicyclo[3.1.0]hexane-2,6-dicarboxylic acid, or a pharmaceutically acceptable salt thereof, which comprises hydrolysing (−)-2-spiro-5'-hydantoinbicyclo[3.1.0]hexane-6-carboxylic acid, which compound has the formula

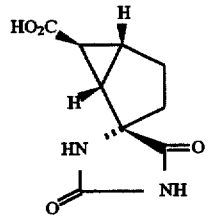
II or a salt thereof, followed if necessary and/or desired by forming a pharmaceutically acceptable salt.

The hydrolysis is preferably performed in the presence of an acid or base as catalyst. Suitable acids include hydrochloric and hydrobromic acid. Suitable bases include alkali metal carbonates and hydroxides, and alkaline earth metal hydroxides, such as sodium carbonate, potassium carbonate, sodium hydroxide, potassium hydroxide, calcium hydroxide and barium hydroxide.

Suitable hydrolysis conditions are further described in G. Kruger, Houben-Weyl, Methoden der Organische Chemie; Vol E5,G. Thieme Verlag: Stuttgart, 1985, pp. 534–546 and S. Kubic et al.; Tetrahedron Letters, 35, 6635(1994).

Preferably the hydrolysis is performed in an aqueous solution, most preferably in water.

The temperature at which the hydrolysis is performed is conveniently in the range of from 0° to 130° C., more preferably from 50° to 110° C.

Heating the compound of formula II under reflux in a 2–4 molar solution of sodium hydroxide has been found to be particularly convenient.

(+)-2-Aminobicyclo[3.1.0]hexane-2,6-dicarboxylic acid may be converted into a pharmaceutically acceptable salt using a conventional technique. It will be appreciated that the compound may form acid addition salts and salts with bases. The acid addition salts are generally prepared by reaction of an acid with the compounds. The salts with bases are generally formed by reaction with a base, for example an alkali metal or alkaline earth metal hydroxide.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically-acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, hippurate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycolate, maleate, tartrate, methanesulfonate, propanesulfonate, naphthalene-1-sulfonate, napthalene-2-sulfonate, mandelate, magnesium, tetramethylammonium, potassium, trimethylammonium, sodium, methylammonium, calcium, and the like salts.

The compound of formula II and its salts are believed to be novel, and are provided as a further aspect of the invention.

Examples of salts of the compound of formula II include salts formed with bases, for example alkali metal salts, such as the sodium or potassium salt, and salts formed with organic amines, for example, 1-phenylethylamine.

The compound of formula II may be prepared by resolution of the corresponding racemic hydantoin, for example by forming a crystalline salt with an optically active amine, such as (R)-1-phenylethylamine.

The racemic hydantoin may be prepared by reacting the compound of formula

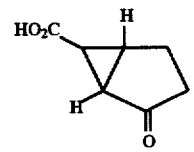
III with an alkali metal cyanide such as sodium or potassium cyanide, and ammonium carbonate. The reaction is conveniently performed in an aqueous solution, such as aqueous ethanol, at a temperature in the range of from 25° to 50° C.

Alternatively, the compound of formula II may be prepared by reacting the chiral compound of formula

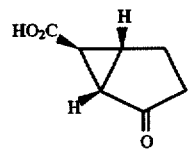
IIIa with an alkali metal cyanide and ammonium carbonate, as described hereinafter.

The compound of formula IIIa may be obtained from the corresponding racemic ketone by resolution, for example, by forming a crystalline salt with (S)-1-phenylethylamine. Suitable solvents include aqueous acetone and mixtures of ethanol and ethyl acetate. An alternative resolving agent, which might be used is quinidine.

The compound of formula III, and the resolved compound of formula IIIa are believed to be novel, and are provided as further aspects of the invention. They may be prepared by hydrolysing the corresponding ethyl ester. This compound may in turn be prepared by reacting an ylide derived from carboethoxymethyl dimethylsulfonium bromide and a base, such as 1,8-diazabicyclo[5.4.0]undec-7-ene, with 2-cyclopenten-1-one. The reaction is conveniently performed in an organic solvent, such as toluene. The temperature is conveniently in the range of from 25° to 50° C.

The following Examples illustrate the invention.

EXAMPLE 1

Carboethoxymethyl Dimethylsulfonium Bromide

A solution of ethyl bromoacetate (265 g) and dimethyl sulfide (114 g) in acetone (500 mL) was stirred at room temperature. After three days, the title compound was isolated by filtration of the reaction mixture. Melting point 88°–90° C.

EXAMPLE 2

(1SR,5RS,6SR) Ethyl 2-Oxobicyclo[3.1.0]hexane-6-carboxylate

A suspension of carboethoxymethyl dimethylsulfonium bromide (45.5 g) in toluene (350 mL) was treated with 1,8-diazabicyclo[5.4.0]undec-7-ene (30.2 g). The resulting mixture was stirred at room temperature. After one hour, the reaction mixture was treated with 2-cyclopenten-1-one (19.57 g). After an additional 18 hours, the reaction mixture was added to a 1N hydrochloric acid/sodium chloride solution. The resulting mixture was extracted with diethyl ether. The combined ether extracts were dried over magnesium sulfate, filtered, and concentrated in vacuo. The residue was purified using silica-gel chromatography, eluting with a linear gradient of 10% ethyl acetate/hexanes to 50% ethyl acetate/hexanes, to give 22.81 g of the title compound. Melting point: 36°–38° C.

FDMS: m/z=168 (M+).

Analysis calculated for $C_9H_{12}O_3$: C, 64.27; H, 7.19. Found: C, 64.54; H, 7.11.

EXAMPLE 3

2-Oxobicyclo[3.1.0]hexane-6-carboxylic acid

A mixture of 60 g of ethyl 2-oxobicyclo[3.1.0]hexane-6-carboxylate and 300 ml of 1N sodium hydroxide was stirred at 25°–30° C. After 2.5 hours, concentrated hydrochloric acid was added to adjust the pH to 0.8–1.2. The resulting solution was extracted with ethyl acetate. The extracts were dried over magnesium sulfate, filtered, and concentrated to give 49.1 g (98%) of the crude material. Recrystallization from 100 ml of ethyl acetate gave the title compound, mp 123.5°–128° C.

FDMS: m/z=140 (M+)

Analysis calculated for $C_7H_8O_3$: C, 60.00; H, 5.75. Found: C, 60.14; H, 5.79.

EXAMPLE 4

2-Oxobicyclo[3.1.0]hexane-6-carboxylic acid salt with (S)-1-phenylethylamine A solution of 14 g of the compound prepared in Example 3 in 140 ml of 25% ethanol in ethyl acetate was combined with (S)-1-phenylethylamine (1 eq.). After stirring overnight, the precipitated salt was isolated by filtration and dried to give 11.87 g (45.4%) of the desired salt. Conversion of the salt to the partially resolved 2-oxobicyclo[3.1.0] hexane-6-carboxylic acid by the method of Example 3 and analysis indicated that the salt was 68% ee. The enantiomeric excess was determined by conversion to the methyl ester with diazomethane followed by chiral HPLC on a Chiralpak AS column at 40° C. eluted with 10% isopropanol/90% hexane at 1 ml/min with detection at 210 nm.

EXAMPLE 5

(+)-2-Oxobicyclo[3.1.0]hexane-6-carboxylic acid

A mixture of 1.31 g of the product of Example 4 and 10 ml of 1N hydrochloric acid was stirred for 5 minutes and extracted with ethyl acetate. The extracts were dried over sodium sulfate, filtered, and concentrated to give 0.61 g of the title compound, mp 110°–115° C. The product was determined to be 68% ee by chiral HPLC (method of Example 4).

FDMS: m/z=141 (M+H)

Optical Rotation: $\alpha_D$=49.85°

EXAMPLE 6

(−)-2-Spiro-5'-hydantoinbicyclo[3.1.0]hexane-6-carboxylic acid

A solution of the compound prepared as described in Example 5 (68% ee, 1 eq.), potassium cyanide (1.25 eq.), and ammonium carbonate (2.5 eq) were combined and stirred in ethanol/water at 25° C. for 40 hours. The mixture was acidified with 6N hydrochloric acid, concentrated, diluted with water, and filtered to give a 79% yield of a 90:10 mixture of diastereomers, mp 286°–290° C. The diastereomeric mixture was recrystallized from isopropanol/water to give in 48% yield the title compound in 100% diastereomeric and 100% enantiomeric purity (enantiomeric ratio determined by chiral HPLC on a 4.6×150 mm Chiralcel OD-H column, eluted with 15% isopropanol/85% hexane at 1 ml/min at 40° C. with detection at 220 nm; diastereomeric ration determined by HPLC on a Zorbax SB-phenyl column at 40° C. with elution with 90:10 buffer/acetonitrile eluted at 2 ml/min with detection at 220 nm (buffer=0.1M dibasic sodium phosphate monohydrate adjusted to pH 2.1 with phosphoric acid).

FDMS: m/z=211 (M+H)

Optical Rotation: $\alpha_D$=−25.98°

Analysis calculated for C9H10N2O4: C, 51.43; H, 4.79; N, 13.33. Found: C, 51.38; H, 4.80; N, 13.26.

EXAMPLE 7

Ethyl 2-spiro-5'-hydantoinbicyclo[3.1.0]hexane-6-carboxylate

A mixture of 5.05 g of ethyl 2-oxobicyclo[3.1.0]hexane-6-carboxylate, 2.15 g of potassium cyanide, 5.77 g of ammonium carbonate, 30 ml of 2B-3 ethanol, and 12 ml of water was stirred at 35° C. until the reaction was complete by HPLC. After 15 hours, the reaction mixture was cooled to 0° C. and 33 ml of water was added to the mixture. After 2 hours at 0° C., the precipitate was isolated by filtration and dried to give 5.23 g (73%) of the title compound, mp 217°–220° C.

FDMS: m/z=238.1 (M+)

Analytical calculated for $C_{11}H_{14}N_2O_4$: C, 55.46; H, 5.92; N, 11.76. Found: C, 55.74; H, 5.88; N, 11.50.

EXAMPLE 8

2-Spiro-5'-hydantoinbicyclo[3.1.0]hexane-6-carboxylic acid

A mixture of 16.32 g of the product of Example 7 and 137 ml of 2N NaOH was stirred at 25° C. After 1 hour, concentrated hydrochloric acid was added to adjust the pH to 1.0. The resulting precipitate was isolated by filtration and dried to give 13.70 g (95%) of the title compound, mp 277°–279° C.

FDMS: m/z=210.1 (M+)

Analysis Calculated for $C_9H_{10}N_2O_4$: C, 51.43; H, 4.79; N, 13.33. Found: C, 51.70; H, 4.93; N, 13.43.

EXAMPLE 9

2-Spiro-5'-hydantoinbicyclo[3.1.0]hexane-6-carboxylic acid, (R)-1-phenylethylamine salt A mixture of 1.05 g of the product of Example 8 and 16.6 ml of a 1.6:1 solution of acetone:water was stirred at 25° C. while adding 1.53 g of R-(+)-1-phenylethylamine. The mixture was stirred for 2 hours at room temperature. The crystals were filtered, rinsed with acetone, and dried to give 0.74 g (45%) of the title compound, mp 205°–212° C.

Optical Rotation: $\alpha_D = -31.88°$ (c=1, methanol)

EXAMPLE 10

(−)-2-Spiro-5'-hydantoinbicyclo[3.1.0]hexane-6-carboxylic acid

A mixture of 0.74 g of the product of Example 9 and 10 ml of water was stirred at 25° C. while the pH was adjusted from 6.81 to 1.0 using 1N HCl. The reaction mixture was stirred for 1 hour and the product was collected by filtration and dried to give 0.35 g (75%) of the title compound, mp 310° C. (decomp).

FDMS: 210.1 (M+)

Optical Rotation: $\alpha_D = -24.22°$ (c=1, methanol)

Analysis calculated for $C_9H_{10}N_2O_4$: C, 51.43; H, 4.80; N, 13.33. Found: C, 51.67; H, 4.87; N, 13.61.

EXAMPLE 11

(+)-2-Aminobicyclo[3.1.0]hexane-2,6-dicarboxylic Acid

A solution of 184 g of (−)-2-spiro-5'-hydantoinbicyclo [3.1.0]-hexane-6-carboxylic acid and 1750 ml of 3N NaOH was heated at reflux until the reaction was complete by HPLC. After 28 hours, the solution was cooled to room temperature and filtered through glass paper to remove trace amounts of insoluble material. The pH of the solution was adjusted to 3.0 using concentrated HCl. The reaction mixture was stirred 1 hour at room temperature and two hours at 0° C. The precipitated product was collected by filtration, washed with 170 ml of cold water and dried to give 152.5 grams (86%) of the title compound.

FDMS: m/z=186.1 (M+1)

Optical rotation: $\alpha_D = 23.18°$ (c=1, 1N HCl)

EXAMPLE 12

2-Oxobicyclo[3.1.0]hexane-6-carboxylic acid salt with (S)-1-phenylethylamine A suspension of 1.0 g of the product of Example 4 and 10 ml of acetone was heated to reflux and combined with 1 ml of water to give a clear solution. On cooling to 5° C., the resulting slurry was filtered, and the collected solid washed with 5 ml of cold 10% water in acetone and dried to give 0.42 g of the title compound. Conversion of a sample of the salt to (+)-2-oxobicyclo[3.1.0]hexane-6-carboxylic acid by the method of Example 5 and analysis indicated that the chiral purity was 90.2% ee. The enantiomeric excess was determined using the method described in Example 4.

EXAMPLE 13

2-Oxobicyclo[3.1.0]hexane-6-carboxylic acid salt with (S)-1-phenylethylamine To 0.7 g of the compound prepared in Example 3 was added at room temperature 7 ml of a solution of 10% water in acetone. The resulting solution was combined at room temperature with (S)-1-phenylethylamine (1 eq.) and 0.5 ml of 10% water in acetone. The reaction mixture was stirred overnight at room temperature, seeded with a few crystals of the salt prepared in Example 12 and stirred an additional 6 hours. The resulting slurry was cooled to 5° C., filtered, and the collected solid was washed with 1.5 ml of 10% water in acetone and dried to give 0.35 g (26.7%) of the title salt. Conversion of a sample of the salt to (+)-2-oxobicyclo [3.1.0]hexane-6-carboxylic acid by the method of Example 5 and analysis indicated that the chiral purity was 92% ee. The enantiomeric excess was determined using the method described in Example 4.

Other solvent combinations can also be used to prepare the (+)-2-oxobicyclo[3.1.0]hexane-6-carboxylic acid salt with (S)-1-phenylethylamine. For example, substitution of 30% ethanol in ethyl acetate for 10% water in acetone gave the title salt in 29% yield and 82% ee.

I claim:

1. A process for the preparation of (+)-2-aminobicyclo [3.1.0]-hexane-2-6-dicarboxylic acid, or a pharmaceutically acceptable salt thereof, which comprises hydrolysing (−)-2-spiro-5'-hydantoinbicyclo[3.1.0]hexane-6-carboxylic acid or a salt thereof, or further forming a pharmaceutically acceptable salt.

2. A process as claimed in claim 1, in which the hydrolysis is performed in the presence of an acid or base as catalyst.

3. A process as claimed in claim 2, in which the catalyst is hydrochloric acid, hydrobromic acid, an alkali metal carbonate, an alkali metal hydroxide or an alkaline earth metal hydroxide.

4. A process as claimed in claim 1, in which the hydrolysis is performed in water.

5. A process as claimed in claim 1, in which the hydrolysis is performed at a temperature in the range of from 0° to 130°.

6. A process as claimed in claim 5, in which the hydrolysis is performed under reflux conditions.

7. (−)-2-spiro-5-hydantoinbicyclo[3.1.0]hexane-6-carboxylic acid, or a salt thereof.

8. A compound as claimed in claim 7 which is (−)-2-spiro-5-hydantoinbicyclo[3.1.0]hexane-6-carboxylic acid or (−)-2-spiro-5-hydantoinbicyclo[3.1.0]hexane-6-carboxylic acid, (R)-1-phenylethylamine salt.

9. 2-oxobicyclo[3.1.0]hexane-6-carboxylic acid, or a salt thereof.

10. A compound as claimed in claim 9, which is (+)-2-oxobicyclo[3.1.0]hexane-6-carboxylic acid or (+)-2-oxobicyclo[3.1.0]hexane-6-carboxylic acid, (S)-1-phenylethylamine salt.

* * * * *